(12) United States Patent
Skraly et al.

(10) Patent No.: US 6,329,183 B1
(45) Date of Patent: Dec. 11, 2001

(54) POLYHYDROXYALKANOATE PRODUCTION FROM POLYOLS

(75) Inventors: Frank A. Skraly, Boston; Oliver P. Peoples, Arlington, both of MA (US)

(73) Assignee: Metabolix, Inc., Cambridge, MA (US)

( * ) Notice: Subject to any disclaimer, the term of this patent is extended or adjusted under 35 U.S.C. 154(b) by 0 days.

(21) Appl. No.: 09/366,920

(22) Filed: Aug. 4, 1999

Related U.S. Application Data

(60) Provisional application No. 60/095,329, filed on Aug. 4, 1998.

(51) Int. Cl.[7] .................................................. C12D 7/62
(52) U.S. Cl. ................................................. 435/135
(58) Field of Search .............................................. 435/135

(56) References Cited

U.S. PATENT DOCUMENTS

| | | |
|---|---|---|
| 4,477,654 | 10/1984 | Holmes et al. . |
| 5,245,023 | 9/1993 | Peoples et al. . |
| 5,502,273 | 3/1996 | Bright et al. . |
| 5,534,432 | 7/1996 | Peoples et al. . |
| 5,602,321 | 2/1997 | John . |
| 5,610,041 | 3/1997 | Somerville et al. . |
| 5,650,555 | 7/1997 | Somerville et al. . |

FOREIGN PATENT DOCUMENTS

| | | |
|---|---|---|
| WO 91/00917 A1 | 1/1991 | (WO) . |
| WO 92/19747 A1 | 11/1992 | (WO) . |
| WO 93/02187 A1 | 2/1993 | (WO) . |
| WO 93/02194 A1 | 2/1993 | (WO) . |
| WO 94/12014 A1 | 6/1994 | (WO) . |
| WO 96/35796 A1 | 11/1996 | (WO) . |
| WO 97/15681 A1 | 5/1997 | (WO) . |
| WO 98/21339 A1 | 5/1998 | (WO) . |
| WO 98/39453 A1 | 9/1998 | (WO) . |
| WO 99/14313 A2 | 3/1999 | (WO) . |

OTHER PUBLICATIONS

Hein, et al., "Biosynthesis of poly(4–hydroxybutyric acid) by recombinant strains of *Escherichia coli*," *FEMS Microbiology Letters* 153:411–18 (1997).
Lee, et al., "Copolymerization of –valerolactone and –butyrolactone," *Eur. Polym. J.* 34:117–22 (1998).
Nawrath, et al., "Targeting of the polyhydroxybutyrate biosynthetic pathway to the plastids of *Arabidopsis thaliana* results in high levels of polymer accumulation," *Proc. Natl. Acad. Sci. USA* 91:12760–64 (1994).
Poirier, et al., "Perspectives on the production of polyhydroxyalkanoates in plants," *Chem. Abs.* 118:11 (1993).
Valentin & Dennis, "Production of poly(3–hydroxybutyrate–co–4–hydroxybutyrate) in recombinant *Escherichia coli* grown on glucose," *J. Biotech.* 58:33–38 (1997).
Yim, et al., "Synthesis of Poly–(3–Hydroxybutyrate–co–3–Hydroxyvalerate) by recombinant *Escherichia coli*," *Biotech. Bioengineer.* 49:495–503 (1996).
Anton, D. "Biological production of 1,3–propanediol", presented at United Engineering Foundation Metabolic Engineering II conference, Elmau, Germany, Oct. 27, 1998.
Bachovchin, et al., "Mechanism of action of adenosylcobalamin: glycerol and other substrate analogues as substrates and inactivators for propanediol dehydratase—kinetics, stereospecificity, and mechanism," *Biochemistry.* 16(6):1082–92 (1977).
Baldoma & Aguilar, "Metabolism of L–fucose and L–rhamnose in *Escherichia coli*: aerobic–anaerobic regulation of L–lactaldehyde dissimilation," *J. Bacteriol.* 170(1):416–21 (1988).
Ben–Amotz, et al., "Glycerol production by Dunaliella," *Experientia* 38:49–52 (1982).
Boenigk, et al., "Fermentation of glycerol to 1,3–propanediol in continuous cultures of *Citrobacter freundii*," *Appl. Microbiol. Biotechnol.* 38:453–57 (1993).
Braunegg, et al., "Polyhydroxyalkanoates, biopolyesters from renewable resources: physiological and engineering aspects," *J. of Biotechnology* 65:127–61 (1998).
Cameron, et al., "Metabolic engineering of propanediol pathways," *Biotechnol. Prog.* 14(1):116–25 (1998).

(List continued on next page.)

Primary Examiner—Charles L. Patterson, Jr.
(74) Attorney, Agent, or Firm—Holland & Knight LLP

(57) ABSTRACT

Organisms are provided which express enzymes such as glycerol dehydratase, diol dehydratase, acyl-CoA transferase, acyl-CoA synthetase β-ketothiolase, acetoacetyl-CoA reductase, PHA synthase, glycerol-3-phosphate dehydrogenase and glycerol-3-phosphatase, which are useful for the production of PHAs. In some cases one or more of these genes are native to the host organism and the remainder are provided from transgenes. These organisms produce poly (3-hydroxyalkanoate) homopolymers or co-polymers incorporating 3-hydroxypropionate or 3-hydroxyvalerate monomers wherein the 3-hydroxypropionate and 3-hydroxyvalreate units are derived from the enzyme catalysed conversion of diols. Suitable diols that can be used include 1,2-propanediol, 1,3 propanediol and glycerol. Biochemical pathways for obtaining the glycerol from normal cellular metabolites are also described. The PHA polymers are readily recovered and industrially useful as polymers or as starting materials for a range of chemical intermediates including 1,3-propanediol, 3-hydroxypropionaldehyde, acrylics, malonic acid, esters and amines.

16 Claims, 4 Drawing Sheets

OTHER PUBLICATIONS

Cazzulo, et al., "On the production of glycerol and $_L$-alanine during the aerobic fermentation of glucose by trypanosomatids," *FEMS Microbiol. Lett.* 51:187–92 (1988).

Dennis, et al., "Formation of poly(3–hydroxybutyrate–co–3–hydroxyhexanoate) by PHA synthase from *Ralstonia eutropha*,"*J. Biotechnol.* 64(2–3):177–86 (1998).

Dobrogosz, et al., "*Lactobacillus reuteri* and the enteric microbiota," in *The Regulatory and Protective Role of the Normal Microflora*, (Grubh, et al., eds.), pp. 283–292, Macmillan Press Ltd., London (1989).

Doi, et al., "Production of biodegradable copolyesters by *Alcaligenes eutrophus*" in *Novel Biodegradable Microbial Polymers*, (Dawes, ed.), Kluwer Academic Publishers: the Netherlands, pp. 37–48 (1990).

Eschenlauer, et al., "Production of heteropolymeric polyhydroxyalkanoate in *Escherichia coli* from a single carbon source," *Int J. Biol. Macromol.* 19(2):121–30 (1996).

Forage & Foster, "Resolution of the coenzyme B–12 dependent dehydratases of Klebsiella sp. and *Citrobacter freundii*," *Biochim. Biophys. Acta.* 569(2):249–58 (1979).

Gancedo, et al., "Glycerol metabolism in yeasts. Pathways of utilization and production," *Eur. J. Biochem.* 5:165–72 (1968).

Casser & Fraley, "Genetically Engineering Plants for Crop Improvement," *Science* 244:1293–99 (1989).

Homann, et al., "Fermentation of glycerol to 1,3–propanediol by Klebsiella and Citrobacter strains," *Appl. Microbiol. Biotechnol.* 33:121–26 (1990).

Legisa & Mattey, "Glycerol synthesis by *Aspergillus niger* under citric acid accumulating conditions," *Enzyme Microb. Technol.* 8:607–09 (1986).

Lin, "Glycerol dissimilation and its regulation in bacteria," *Annu. Rev. Microbiol.* 30:535–78 (1976).

Lu, et al., "Fermentation of xylose to glycerol by *Rhizopus javanicus*," *Appl. Biochem. Biotechnol.* 51/52:83–95 (1995).

Fukui, et al., "Biosynthesis of poly(3–hydroxybutyrate–co–3–hydroxyvalerate–co–3–hydroxyheptanoate) terpolymers by recombinant *Alcaligenes eutrophus*," *Biotechnol. Lett.*¯19:1093–97 (1997).

Madison & Huisman, "Metabolic engineering of poly(3–hydroxyalkanoates): from DNA to plastic," *Microbiology and Molecular Biology Reviews* 63:21–53 (1999).

Miller, *A short course in bacterial genetics*, Cold Spring Harbor Laboratory Press, Cold Spring Harbor, NY (1992). (Index only).

Moezelaar, et al., "Fermentation and sulfur reduction in the mat–building cyanobacterium *Microcoleus chthonoplastes*," *Appl. Environ. Microbiol.* 62:1752–58 (1996).

Neish, et al., "Dissimilation of glucose by *Bacillus subtilis* (Ford's Strain)," *Can. J. Res.* 23B:290–96 (1945).

Nelson & Werkman, "Dissimilation of glucose by heterofermentative lactic acid bacteria," *J. Bacteriol.* 30:547–57 (1935).

Owen, et al., *Transgenic Plants: A Production System for Industrial and Pharmaceutical Proteins* John Wiley & Sons Co.: England, 1996. (Index only).

Peoples & Sinskey, "Poly–beta–hydroxybutyrate (PHB) biosynthesis in *Alcaligenes eutrophus* H16. Identification and characterization of the PHB polymerase gene (phbC)," *J. Biol. Chem.* 264(26):15298–03 (1989).

Poirier, "Production of new polymeric compounds in plants," *Current Opinion in Biotechnology* 10:181–85 (1999).

Poirier, et al., "Polyhydroxybutyrate, a biodegradable thermoplastic, produced in transgenic plants," *Science* 256:520–23 (1992).

Potrykus & Spangenberg, *Gene Transfer to Plants,* Springer–Verlag:Berlin Heidelberg New York, 1995. (Index only).

Skraly, et al., "Construction and characterization of a 1,3–propanediol operon," *Appl. Environ. Microbiol.* 64(1):98–105 (1998).

Slater, et al., "Multiple beta–ketothiolases mediate poly(beta–hydroxyalkanoate) copolymer synthesis in *Ralstonia eutropha*," *J. Bacteriol.* 180(8):1979–87 (1998).

Söhling & Gottschalk, "Molecular analysis of the anaerobic succinate degradation pathway in *Clostridium kluyveri*," *J. Bacteriol.* 178:871–80 (1996).

Spratt, et al., "Isolation and genetic characterization of *Escherichia coli* mutants defective in propionate metabolism," *J. Bacteriol.* 146(3):1166–69 (1981).

Sridhara, et al., "Ferrous–activated nicotinamide adenine dinucleotide–linked dehydrogenase from a mutant of *Escherichia coli* capable of growth on 1,2–propanediol," *J. Bacteriol.* 98(1):87–95 (1969).

Steinbüchel & Müller, "Glycerol, a metabolic end product of *Trichomonas vaginalis* and *Tritrichomonas foetus*," *Mol. Biochem. Parasitol.* 20(1):45–55 (1986).

Steinbüchel, et al., "Synthesis and production of poly(3–hydroxyvaleric acid) homopolyester by *Chromobacterium violaceum*," *Appl. Microbiol. Biotechnol.* 39:443–49 (1993).

Streekstra, et al., "Overflow metabolism during anaerobic growth of *Klebsiella aerogenes* NCTC 418 on glycerol and dihydroxyacetone in chemostat culture," *Arch. Microbiol.* 147:268–75 (1987).

Sussman & Avron, "Characterization and partial purification of $_{DL}$–Glycerol–1–phosphatase from *Dunaliella salina*," *Biochim. Biophs. Acta* 661:199–204 (1981).

Tonino & Steyn–Parvé, "Localization of some phosphatases in yeast," *Biochim. Biophys. Acta* 67:453–69 (1963).

Tsuboi & Hudson, "Acid Phoshatase. VI. Kinetic properties of purifed yeast and erythrocyte phosphomonoesterase," *Arch. Biochem. Biophys.* 61:197–10 (1956).

Valentin, et al., "Cloning and characterization of the *Methylobacterium extorquens* polyhydroxyalkanoic–acid–synthase structural gene," *Appl. Microbiol. Biotechnol.* 39(3):309–17 (1993).

Van Schaftingen & Van Laere, "Glycerol formation after the breaking of dormancy of *Phycomyces blakesleeanus* spores. Role of an interconvertible glycerol–3–phosphatase," *Eur. J. Biochem.* 148(2):399–404 (1985).

Viikari, "Carbohydrate metabolism in zymononas," *CRC Crit. Rev. Biotechnol.* 7:237–61 (1988).

Wassef, et al., "Utilization of glycerophosphate for phospholipid synthesis by cells of *Halobacterium cutirubrum*," *Can. J. Biochem.* 48(1):63–67 (1970).

Williams & Peoples, "Biodegradable plastics from plants," *CHEMTECH* 38–44 (1996).

Zhang, et al., "Production of polyhydroxyalkanoates in sucrose–utilizing recombinant *Escherichia coli* and Klebsiella strains," *Appl. Environ. Microbiol.* 60(4):1198–1205 (1994).

SEQUENCE LISTING

```
<160> NUMBER OF SEQ ID NOS:  8

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 1
tcccctagga ttcaggaggt ttttatggag tgggaagaga tatataaag              49

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 2
ccttaagtcg acaaattcta aaatctcttt ttaaattc                          38

<210> SEQ ID NO 3
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 3
cttccggatc cattcaggag gttttatgt ctgctgctgc tgataga                 47

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 4
cttccgcggc cgcctaatct tcatgtagat ctaattc                           37

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 5
cttccgcggc cgcattcagg aggtttttat gggattgact actaaacctc             50
```

```
<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 6
ccttctcgag ttaccatttc aacagatcgt cc                              32

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 7
ggtggtacct taagaggagg tttttatgaa ttttcatcac ctggctt              47

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 8
ggtgcggccg ctcaggcctc caggcttatc ca                              32
```

POLYHYDROXYALKANOATE PRODUCTION FROM POLYOLS

CROSS-REFERENCE TO RELATED APPLICATIONS

Priority is claimed to U.S. provisional application Ser. No. 60/095,329 filed Aug. 4, 1998.

BACKGROUND OF THE INVENTION

This is generally in the field of production of polyhydroxyalkanoates by genetic engineering of bacterial enzymes.

Numerous microorganisms have the ability to accumulate intracellular reserves of poly [(R)-3-hydroxyalkanoate] (PHA) polymers. PHAs are biodegradable and biocompatible thermoplastic materials with a broad range of industrial and biomedical applications (Williams and Peoples, 1996, CHEMTECH 26: 38–44). PHAs can be produced using a number of different fermentation process and recovered using a range of extraction techniques (reviewed by Braunegg et al. 1998, J. Biotechnol. 65: 127–161; Choi and Lee, 1999). Plant crops are also being genetically engineered to produce these polymers offering a cost structure in line with the vegetable oils and direct price competitiveness with petroleum-based polymers (Williams and Peoples 1996, CHEMTECH 26:38–44; Poirier, Y. 1999, Plant Biotechnology pp. 181–185). PHAs are formed by the action of a PHA synthase enzyme. As the polymer chains grow, they form insoluble granules. The PHAs can then be recovered and then converted into chemicals or converted into chemicals during the recovery process (Martin et al. PCT WO 97/15681). Therefore, in addition to their utility as polymers, the PHAs represent a unique mechanism for storing new chemistries in both microbial and plant crop systems.

PHA copolymers containing 3-hydroxyvalerate (3HV), especially PHBV, have been described extensively. Many wild type microorganisms are capable of producing 3HV-containing PHAs. PHBV has been produced commercially using *Ralstonia eutropha* (formerly *Alcaligenes eutrophus*) from glucose and propionate and from glucose and isobutyrate (U.S. Pat. No. 4,477,654 to Holmes et al.). A number of other microorganisms and processes are known to those skilled in the art (Braunegg et al. 1998, Journal of Biotechnology 65: 127–161). Poly(3HV) homopolymer has been produced using *Chromobacterium violaceum* from valerate (Steinbüchel et al., 1993, Appl. Microbiol. Biotechnol. 39:443–449). PHAs containing 3HV units have also been synthesized using recombinant microorganisms. *Escherichia coli* harboring the *R. eutropha* PHA biosynthesis genes has been used to produce PHBV from glucose and either propionate or valerate (Slater et al., 1992, Appl. Environ. Microbiol. 58:1089–1094) and from glucose and either valine or threonine (Eschenlauer et al., 1996, Int. J. Biol. Macromol. 19:121–130). Klebsiella oxytoca harboring the *R. eutropha* PHA biosynthesis genes has been used to produce PHBV from glucose and propionate (Zhang et al., 1994, Appl. Environ. Microbiol. 60:1198–1205). *R. eutropha* harboring the PHA synthase gene of *Aeromonas caviae* was used to produce poly(3HV-co-3HB-co-3HHp) from alkanoic acids of odd carbon numbers (Fukui et al., 1997, Biotechnol. Lett. 19:1093–1097).

PHA copolymers containing 3-hydroxypropionate units have also been described. Holmes et al. (U.S. Pat. No. 4,477,654) used *R. eutropha* to synthesize poly(3HP-co-3HB-co-3HV) from glucose and either 3-chloropropionate or acrylate. Doi et al. (1990, in E. A. Dawes (ed.), *Novel Biodegadable Microbial Polymers*, Kluwer Academic Publishers, the Netherlands, pp. 37–48) used *R. eutropha* to synthesize poly(3HP-co-3HB) from 3-hydroxypropionate, 1,5-pentanediol, 1,7-heptanediol, or 1,9-nonanediol. Hiramitsu and Doi (1993, Polymer 34:4782–4786) used *Alcaligenes latus* to synthesize poly(3HP-co-3HB) from sucrose and 3-hydroxypropionate. Shimamura et al. (1994, Macromolecules 27: 4429–4435) used *A. latus* to synthesize poly(3HP-co-3HB) from 3-hydroxypropionate and either 3-hydroxybutyrate or sucrose. The highest level of 3-hydroxypropionate incorporated into these copolymers was 88 mol % (Shimamura et al., 1994, ibid.). No recombinant 3HP containing PHA producers have been described in the art.

It is economically desirable to be able to produce these polymers in transgenic crop species. Methods for production of plants have been described in U.S. Pat. No. 5,245,023 and U.S. Pat. No. 5,250,430; U.S. Pat. No. 5,502,273; U.S. Pat. No. 5,534,432; U.S. Pat. No. 5,602,321; U.S. Pat. No. 5,610,041; U.S. Pat. No. 5,650,555: U.S. Pat. No. 5,663,063; WO 9100917, WO 9219747, WO 9302187, WO 9302194 and WO 9412014, Poirier et.al., 1992, Science 256; 520–523, Williams and Peoples, 1996, Chemtech 26, 38–44, the teachings of which are incorporated by reference herein). In order to achieve this goal, it is necessary to transfer a gene, or genes in the case of a PHA polymerase with more than one subunit, encoding a PHA polymerase from a microorganism into plant cells and obtain the appropriate level of production of the PHA polymerase enzyme. In addition it may be necessary to provide additional PHA biosynthetic genes, e.g. a ketoacyl-CoA thiolase, an acetoacetyl-CoA reductase gene, a 4-hydroxybutyryl-CoA transferase gene or other genes encoding enzymes required to synthesize the substrates for the PHA polymerase enzymes. In many cases, it is desirable to control the expression in different plant tissues or organelles. Methods for controlling expression in plant tissues or organelles are known to those skilled in the art (Gasser and Fraley, 1989, Science 244; 1293–1299; Gene Transfer to Plants,1995, Potrykus, I. and Spangenberg, G. eds. Springer-Verlag Berlin Heidelberg New York. and "Transgenic Plants: A Production System for Industrial and Pharmaceutical Proteins", 1996, Owen, M. R. L. and Pen, J. Eds. John Wiley & Sons Ltd. England, incorporated herein by reference).

Although methods for production of a variety of different copolymers in bacterial fermentation systems are known, and production of PHAs in plants has been achieved, the range of copolymers possible in bacteria has not been achieved in plants. It would be advantageous to be able to produce different copolymers in transgenic plants, and to have more options with regard to the substrates to be utilized by the transgenic plants.

It is therefore an object of the present invention to provide methods and reagents for production of PHAs in plants.

It is a further object of the present invention to provide methods and reagents for production of PHAs using simple sugars and alcohols as substrates.

It is still another object of the present invention to provide methods and reagents for production of copolymers other than PHB and PHVB.

SUMMARY OF THE INVENTION

Organisms are provided which express enzymes such as glycerol dehydratase, diol dehydratase, acyl-CoA transferase, acyl-CoA synthetase β-ketothiolase, acetoacetyl-CoA reductase, PHA synthase, glycerol-3- phosphate dehydrogenase and glycerol-3-phosphastase, which are useful for the production of PHAs. In some cases one or more of these genes are native to the host organism and the remainder are provided from transgenes. These organisms produce poly (3-hydroxyalkanoate) homopolymers or co-polymers incorporating 3-hydroxypropionate or 3-hydroxyvalerate monomers wherein the 3-hydroxypropionate and 3-hydroxyvalreate units are derived from the enzyme catalysed conversion of diols. Suitable diol; that can be used include 1,2-propanediol, 1,3propanediol and glycerol. Biochemical pathways for obtaining the glycerol from normal cellular metabolites are also described. The PHA polymers are readily recovered and industrially useful as polymers or as starting materials for a range of chemical intermediates including 1,3-propanediol, 3-hydroxypropionaldehyde, acrylics, malonic acid, esters and amines.

DETAILED DESCRIPTION OF THE INVENTION

New metabolic pathways have been developed for the production of PHAs containing 3-hydroxyvalerate units from 1,2-propanediol and of PHAs containing 3-hydroxypropionate units from 1,3 propanediol or glycerol. In the case of glycerol, the glycerol can either be fed to the microorganism or can be produced from central metabolic intermediates . The key enzymes components of these novel metabolic pathways leading to these monomers and their polymerization are illustrated in FIG. 1.

1,2-propanediol and glycerol are inexpensive substrates that are non toxic to many microorganisms even at high concentrations. 1,3-propanediol can be produced from renewable resources (Anton, D. "Biological production of 1,3-propanediol", presented at United Engineering Foundation Metabolic Engineering II conference, Elmau, Germany, Oct. 27, 1998). 1,2-propanediol is present in industrial waste streams from production of propylene glycol. Glycerol can also be obtained from metabolism in a number of microbes and plant crops. In many cases, these are superior feedstocks for fermentation as compared to organic acids, which generally become toxic at low concentrations to many microorganisms. 3-Hydroxypropionic acid is not chemically stable and therefore is not commercially available.

Organisms to be Engineered

Figure 1:
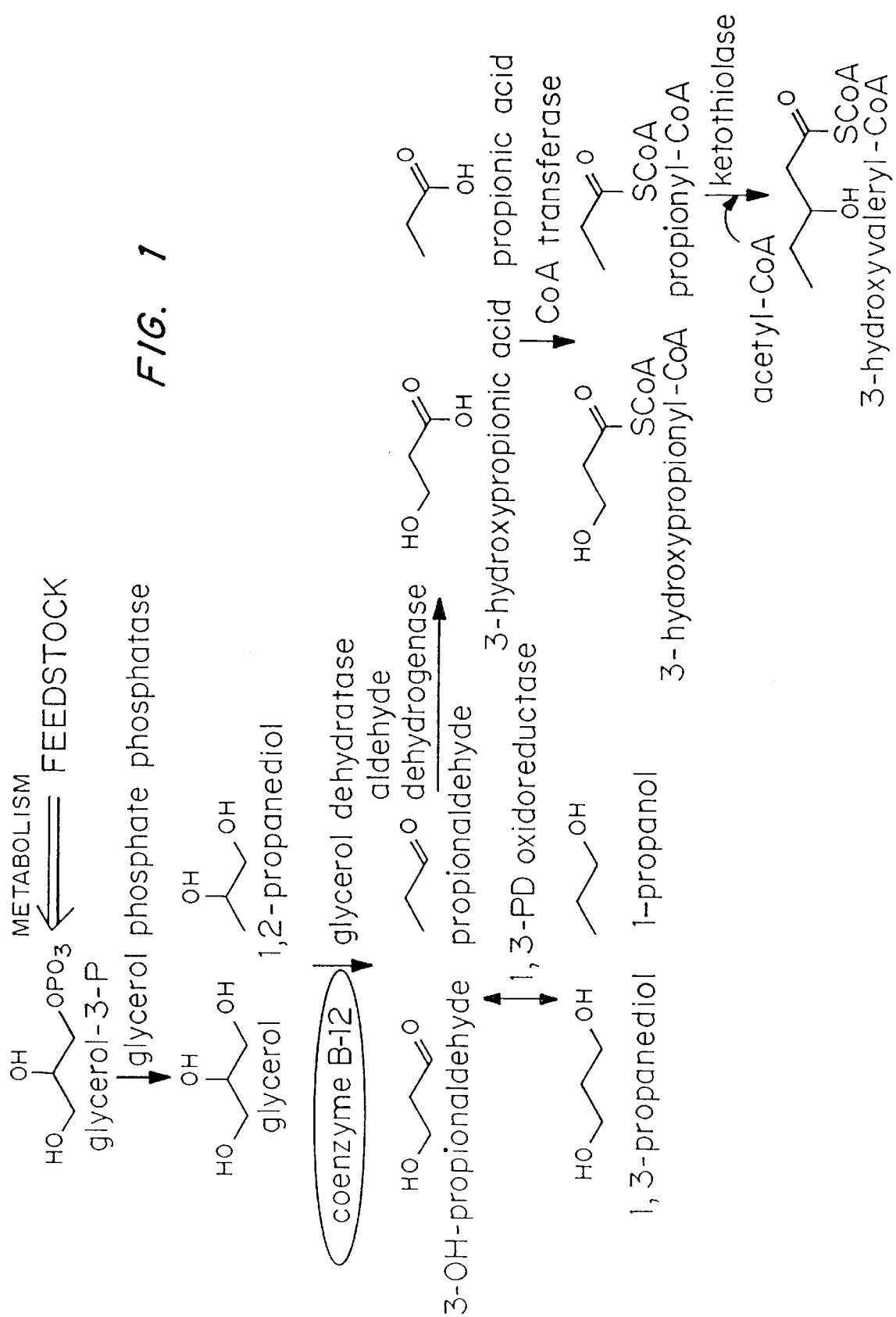
FIG. 1 is a flow chart of the production of 3-hydroxyvaleryl-CoA from glycerol-3-P.

In one embodiment, genes for the entire pathway illustrated in FIG. 1 are introduced into the production organism. An organism, that does not naturally produce PHAs, such as *Escherichia coli*, may be used. A number of recombinant *E. coli* PHB production systems have been described (Madison and Huisman, 1999, Microbiology and Molecular Biology Reviews, 63: 21–53). The genes encoding a vicinal diol dehydratase, from an organism that naturally can convert glycerol to 3-hydroxypropionaldehyde (*Klebsiella pneumoniae*, e.g.), are introduced into this host. In the case of 1,2-propanediol, the vicinal diol dehydratase converts the substrate to propionaldehyde, which can be converted to propionyl-CoA by the endogenous metabolism of the microorganism, optionally with the aid of an exogenous acyl-CoA transferase or acyl-CoA synthetase. It may be useful to mutagenize and select strains with increased resistance to propionaldehyde. Propionyl-CoA can then oe accepted by the ketoacyl-CoA thiolase in a condensation with acetyl-CoA, thus forming 3-hydroxyvaleryl-CoA. The ketoacyl-CoA thiolase will also condense acetyl-CoA with acetyl-CoA, thus forming 3-hydroxybutyryl-CoA. Both 3-hydroxyvaleryl-CoA and 3-hydroxybutyryl-CoA can be accepted by various PHA synthases such as the one expressed in the recombinant host, and therefore PHBV is synthesized by the recombinant host.

The host described above can also be fed 1,3 propanediol or glycerol either during growth or after a separate growth phase, and a 3HP polymer is accumulated within the cells. *E. coli* does not synthesize coenzyme B-12 de novo, and therefore coenzyme B-12 or a precursor that *E. coli* can convert to coenzyme B-12, such as vitamin B-12, must also be fed. In the case of glycerol, the vicinal diol dehydratase converts the substrate to 3-hydroxypropionaldehyde, which can be converted to 3-hydroxypropionyl-CoA by the endogenous metabolism of the microorganism, optionally with the aid of an exogenous acyl-CoA transferase or acyl-CoA synthetase. 3-Hydroxypropionyl-CoA may then be polymerized by PHA synthase to P3HP. Hydroxyacyl-CoA monomer units in addition to 3HP may also be incorporated into the polymer. If ketoacyl-CoA thiolase and reductase are expressed, for example, then a copolymer of 3-hydroxybutyrate and 3-hydroxypropionate can be formed.

In order to produce the 3HP polymers directly from carbohydrate feedstocks, the *E. coli* is further engineered to express glycerol-3-phosphate dehydrogenase and glycerol-3-phosphatase. Such recombinant *E. coli* strains and methods for their construction are known in the art (Anton, D. "Biological production of 1,3-propanediol", presented at United Engineering Foundation Metabolic Engineering II conference, Elmau, Germany, Oct. 27, 1998; PCT WO 98/21339).

In another embodiment, a recombinant organism that naturally contains a vicinal diol dehydratase can be used. One example of such an organism is *Klebsiella oxytoca*, although several others exist, as discussed above. In this embodiment no exogenous vicinal diol dehydratase need be imported from another organism. However it may be useful to mutagenise this organism and select mutants that express the dehydratase during aerobic growth or it can be genetically engineered to express the gene uider aerobic conditions. It is generally the case that organisms which contain one or more coenzyme B-12-dependent vicinal diol dehydratases can synthesize coenzyme B-12 de novo, and in those cases it is not necessary to add coenzyme B-12 or closely related precursors thereof to any part of the cultivation. In this case, a PHA synthase or an entire PHB biosynthetic pathway and optionally an exogenous acyl-CoA transferase or acyl-CoA synthetase is introduced into this organism. Techniques for doing this are well known in the art (for example, Dennis et al., 1998, Journal of Biotechnology 64: 177–186). In order to produce the 3HP polymers directly from carbohydrate feedstocks, the strain is further engeneered to express glycerol-3-phosphate dehydrogenase and glycerol-3-phosphatase as described above.

In another embodiment, an organism that naturally produces PHAs can be used. Examples of such organisms include *Ralstonia eutropha, Alcaligenes latus* and *Azotobacter* but many others are well-known to those skilled in the art (Braunegg et al. 1998, Journal of Biotechnology 65: 127–161). The introduction of the diol dehydratase is accomplished using standard techniques as described by Peoples and Sinskey (1989, J. Biol. Chem. 164, 15298–15303). In these cases it may be useful to mutate the organism and select for increased resistance to 3-hydroxypropionaldehyde. PHA-producing organisms vary in their ability to synthesize coenzyme B-12 de novo, and therefore coenzyme B-12 or a precursor which the organism can convert to coenzyme B-12 would be added as appropriate. PHBV is then produced by feeding 1,2 propanediol and at least one other feedstock. PHBP is produced by feeding 1,3 propanediol or glycerol and one other feedstock, for example, glucose. In order to produce the 3HP polymers directly from carbohydrate feedstocks, the strain is further engineered to express glycerol-3-phosphate dehydrogenase and glycerol-3-phosphatase as described above. It may be useful to utilize mutations that are beneficial for the production of the P3HP homopolymers in these organisms. Specific mutations include inactivating the β-ketothiolase and/or acetoacetyl-CoA reductase genes. As these genes are generally well known and available or isolatable, gene disruptions can be readily carried out as described for example by Slater et. al., 1998 (J. Bacteriol.) 180(8): 1979–87.

The implementation of the production of poly(3-hydroxypropionate) and its copolymers is also not limited to bacteria as described in the examples. The same genes may be introduced into eukaryotic cells, including but not restricted to, yeast and plants, which, like bacteria, also produce glycolytic intermediates such as dihydroxyacetone phosphate, from which glycerol and ultimately poly(3-hydroxypropionate) may be derived.

Genes for Utilization of Substrates

Genes and techniques for developing recombinant PHA producers suitable for use as described herein are generally known to those skilled in the art (Madison and Huisman, 1999, Microbiology and Molecular Biology Reviews, 63: 21–53; PCT WO 99/14313, which are incorporated herein by reference). Because all of the genes necessary to implement the production of poly(3-hydroxypropionate) from central metabolic intermediates via glycerol have been cloned and are available in genetically manipulatable form, any combination of plasmid-borne and integrated genes may be used, and the implementation of this pathway is therefore not restricted to the schemes outlined herein. Many different implementations will be apparent to those skilled in the art.

Glycerol dehydratase (EC 4.2.1.30) and diol dehydratase (EC 4.2.1.28) are distinct coenzyme B-12-requiring enzymes found in several species of bacteria. Often glycerol dehydratase is induced during anaerobic growth on glycerol and diol dehydratase is induced during anaerobic growth on either glycerol or 1,2-propanediol (Forage and Foster, 1979, Biochim. Biophys. Acta 569:249–258). These dehydratases catalyze the formation of 3-hydroxypropionaldehyde from glycerol and propionaldehyde from 1,2propanediol. These aldehydes are usually converted to the corresponding alcohols by a dehydrogenase. Organisms that contain one or both dehydratases typically are able to convert glycerol to 3-hydroxypropionaldehyde or 1,3-propanediol. Bacterial species noted for this ability include *Klebsiella pneumoniae* (Streekstra et al., 1987, Arch. Microbiol. 147: 268–275), *Klebsiella oxytoca* (Homann et al., 1990, Appl. Microbiol. Biotechnol. 33: 121–126), *Klebsiella planticola* (Homann et al., 1990, ibid.) and *Citrobacter freundii* (Boenigk et al., 1993, Appl. Microbiol. Biotechnol. 38: 453–457) although many other examples are generally known. Both dehydratases are formed of three subunits, each of which is homologous to its counterpart in the other enzyme.

The substrate range of the glycerol and diol dehydratases (which will also be referred to generically from this point on as "vicinal diol dehydratases") is not limited to glycerol and 1,2-propanediol. Bachovchin et al. (1977, Biochemistry 16:1082–1092), for example, demonstrated that the substrates accepted by the *K pneumoniae* enzyme include glycerol, (R)-1,2-propanediol, (S)-1,2-propanediol, ethylene glycol, thioglycerol, 3-chloro-1,2-propanediol, 1,2-butanediol, 2,3-butanediol, isobutylene glycol, and 3,3,3,trifluoro-1,2-propanediol. In all cases, the product of the reaction is the aldehyde or ketone formed by the effective removal of a water molecule from the substrate.

Organisms that naturally produce glycerol from sugars through phosphoglycerate include *Bacillus licheniformis* (Neish et al., 1945, Can. J. Res. 23B: 290–296), *Lactobacillus sp.* (Nelson and Werkman, 1935, J. Bacteriol. 30: 547–557), *Halobacterium cutirubrum* (Wassef et al., 1970, Can. J. Biochem. 48: 63–67), *Microcoleus chthonoplastes* (Moezelaar et al., 1996, Appl. Environ. Microbiol. 62: 1752–1758), *Zymomonas mobilis* (Viikari, 1988, CRC Crit. Rev. Biotechnol. 7:237–261), *Phycomyces blakesleeanus* (Van Schaftiger. and Van Laere, 1985, Eur. J. Biochem. 148: 399–405), *Saccharomyces cerevisiae* (Tsuboi and Hudson, 1956, Arch. Biochem. Biophys. 61: 197–210), *Saccharomyces carlsbergensis* (Tonino and Steyn-Parvé, 1963, Biochim. Biophys. Acta 67: 453–469), *Rhizopus javanicus* (Lu et al., 1995, Appl. Biochem. Biotechnol. 51/52: 83–95), *Candida magnoliae* (Sahoo, D. K., 1991, Ph.D. Thesis, Indian Institute of Technology, Delhi), *Candida utilis* (Gancedo et al., 1968, Eur. J. Biochem. 5: 165–172), *Aspergillus niger* (Legisa and Mattey, 1986, Enzyme Microb. Technol. 8: 607–609), *Trichomonas vaginaiis* (Steinbüchel and Müller, 1986, Molec. Biochem. Parasitol. 20: 45–55), *Dunaliella salina* (Sussman and Avron, 1981, Biochim. Biophys. Acta 661: 199–204; Ben-Amotz et al., 1982, Experientia 38: 49–52), *Asteromonas gracilis* (Ben-Amotz et al., ibid.), *Leishmania mexicana* (Cazzulo et al., 1988, FEMS Microbiol. Lett. 51: 187–192), and *Crithidia fasciculata* (Cazzulo et al., ibid.). In many of these organisms, glycerol is known to be derived from dihydroxyacetone phosphate, an intermediate of the glycolytic pathway. *Escherichia coli* does not normally synthesize glycerol in significant amounts when grown on most sugars (Baldomà and Aguilar, J. Bacteriol. 170:416, 1988). However, transgenic *E. coli* strains that can form glycerol from common sugars such as glucose have been described, for example, in PCT WO 97/20292.

Genetically engineered systems for the production of glycerol from sugars (WO 98/21339), the production of 1,3-propanediol from glycerol (WO 96/35796, WO 98/21339) and the production of 1,3-propanediol from sugars have been described. *E. coli* expressing the DAR1 (dihydroxyacetone phosphate dehydrogenase) and GPP2 (sn-glycerol-3-phosphate phosphatase) genes of *Saccharomyces cerevisiae* were shown to accumulate high concentrations of glycerol in the medium when grown on glucose (Anton, D. "Biological production of 1,3-propanediol", presented at United Engineering Foundation Metabolic Engineering II conference, Elmau, Germany, Oct. 27, 1998).

Regulation of Expression

In any of the aforementioned embodiments, it is possible to control the composition of the polymer produced by controlling the expression of the vicinal diol dehydratase or by controlling the availability of coenzyme B-12. The higher the dehydratase activity, the more activated mcnomer will be derived as a result of its activity, up to the point where another factor such as substrate availability or an enzyme activity downstream of the dehydratase becomes limiting. Methods for modulation of gene expression (and thus enzyme activity) in various organisms are well-known to those skilled in the art. An additional method for the control of vicinal diol dehydratase activity is the modulation of the availability of coenzyme B-12 to the microorganism. Many strains of *Escherichia coli*, for example, are unable to synthesize coenzyme B-12 de novo, and therefore recombinant vicinal diol dehydratase, which depends upon coenzyme B-12 for activity, is not active in these strains unless coenzyme B-12 or a suitable precursor such as vitamin B-12 is added to the medium. In *Escherichia coli* strains which harbor PHA synthesis genes and a vicinal diol dehydratase, it has been found that with no coenzyme B-12 addition, only PHB is synthesized even though 1,2-propanediol is present in the medium. The addition of 1 $\mu$M coenzyme B-12 to a cultivation of the same strain in the same medium leads to PHBV formation as discussed in the examples. Skraly et al. (1998, Appl. Environ. Microbiol. 64:98–105) found that transgenic *Escherichia coli* synthesized increasing levels of 1,3-propanediol from glycerol as increasing concentrations of coenzyme B-12 were provided in the medium, up to a concentration of about 20 nM, after which the 1,3-propanediol yield did not increase. Therefore, coenzyme B-12 concentrations from 0 to 20 nM can be used to control the PHBV composition in *Escherichia coli* harboring PHA synthesis genes and a vicinal diol dehydratase gene cultivated in a medium containing 1,2-propanediol. The same basic premise is true for deriving poly(3-hydroxypropionate) from glycerol. The cells are able to make a PHA (such as PHB) in the presence of comonomer when no vicinal diol dehydratase is present. The use of coenzyme B-12 to control polymer composition can be accomplished with any microorganism tfat is unable to synthesize coenzyme B-12 de novo. Such organisms include those that naturally lack this ability (such as *Escherichia coli*) and those that naturally possess this ability (such as *Klebsiella pneumoniae*) but have been mutated by the use of chemical mutagenesis or by genetic methods such as transposon mutagenesis to lose this ability.

In the case of some microorganisms, some of the genes can be integrated into the host chromosome and others provided on a plasmid. In some cases, compatible plasmid systems can be used, for example, with sevtral steps on the pathway encoded on one plasmid and the other steps encoded by a second plasmid. A combination of the two approaches may also be used.

Substrates

As discussed above, substrates that can be used to make PHAs include glycerol and glucose. A number of other substrates, in addition to glycerol or glucose, can be used successfully. Examples of other substrates include starch, sucrose, lactose, fructose, xylose, galactose, corn oil, soybean oil, tallow, tall oil, fatty acids or combinations thereof.

The present invention will be further understood by reference to the following non-limiting examples.

EXAMPLE 1

PHBV Production from Glucose and 1,2-propanediol

Figure 2:
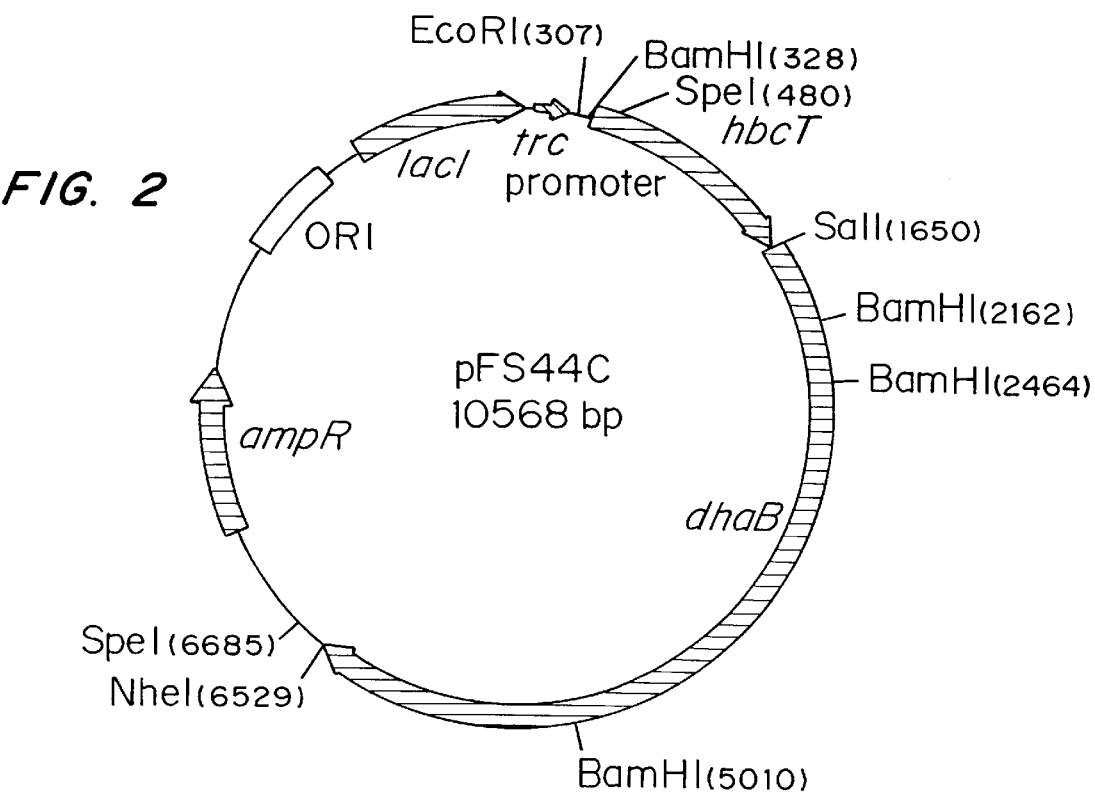
FIG. 2 is a schematic of the plasmid construct pFS44C encoding glycerol dehydratase (dhaB) and 4-hydroxybutyryl-CoA transferase (hbcT).

*Escherichia coli* strain MBX769 (Huisman et. al. PCT WO 99/14313), which expresses the PHA synthesis genes from *Zogloea ramigera* (acetoacetyl-CoA thiolase, acetoacetyl-CoA reductase, and PHA synthase) containing plasmid pFS44C was used to synthesize PHBV from glucose and 1,2-propanediol. Plasmid pFS44C (shown schematically in FIG. 2) contains the genes encoding *Klebsiella pneumoniae* glycerol dehydratase (dhaB), isolated from pTC53 (Skraly et al., 1998, Appl. Environ. Microbiol. 64:98–105), and the *Clostridium kluzyveri* 4-hydroxybutyryl-CoA transferase (hbcT), isolated from pCK3 (Söhling and Gottschalk, 1996, J. Bacteriol. 178:871–880), both in one operon under control of the trc promoter. pFS44C also contains the lac repressor gene (lacl), an ampicillin resistance gene (ampR), and an origin of replication (ORI), all derived from the vector pSE380 (Invitrogen; La Jolla, Calif.).

The cells were precultured in 100 mL of a medium containing 25 g/L of LB broth powder (Difco; Detroit, Mich.) and 100 mg/L ampicillin. They were removed from this medium by centrifugation (2000×g, 10 minutes) and resuspended in 100 mL of a medium containing, per liter: 5 g LB broth powder; 50 mmol potassium phosphate, pH 7; 10g 1,2-propanediol; 2 g glucose; 1 $\mu$mol coenzyme B-12; 100 $\mu$g ampicillin; and 0.1 mmol isopropyl-$\beta$-D-thiogalactopyranoside (IPTG). The cells were incubated in this medium with shaking at 225 rpm at 30° C. for 48 hours. They were then removed by centrifugation as above, washed once with water, and lyophilized.

The same experiment was done in parallel, except that no coenzyme B-12 was added. About 25 mg of lyophilized cell mass from each flask was subjected to simultaneous extraction and butanolysis at 110° C. for 3 hours in 2 mL of a mixture containing (by volume) 90% 1-butanol and 10% concentrated hydrochloric acid, with 2 mg/mL benzoic acid added as an internal standard. The water-soluble components of the resulting mixture were removed by extraction with 3 mL water. The organic phase (1 $\mu$L at a split ratio of 1:50 at an overall flow rate of 2 mL/min) was analyzed on an SPB-1 fused silica capillary GC column (30 m; 0.32 mm ID; 0.25 $\mu$m film; Supelco; Bellefonte, Pa.) with the following temperature profile: 80° C., 2 min; 10° C. per min to 250° C.; 250° C., 2 min. The standard used to test for the presence of 3-hydroxybutyrate and 3-hydroxyvalerate units in the polymer was PHBV (Aldrich Chemical Co.; Milwaukee, Wis.). The polymer in the experiment with coenzyme B-12 added accounted for 60.9% of the dry cell weight, and it was composed of 97.4% 3-hydroxybutyrate units and 2.6% 3-hydroxyvalerate units.

The supernatant at the conclusion of this experiment was found by high-performance performance liquid chromatographic (HPLC) analysis to contain 0.41 g/L propanol, indicating that the glycerol dehydratase was. fimctional. The polymer in the experiment with no coenzyme B-12 added accounted for 56.7% of the dry cell weight, and it was PHB homopolymer. The supernatant at the conclusion of this experiment did not contain propanol. HPLC analysis was done with an Aminex HPX-87H column with sulfuric acid (pH 2) as the mobile phase at a flow rate of 0.6 mL/min and a column temperature of 50° C. Detection was by both refractive index and ultraviolet absorption.

EXAMPLE 2

PHBV and growth from 1,2-propanediol as sole carbon source

MBX 184 was selected for growth on 1,2-PD, to yield *E. coli* strain MBX 1327. MBX1327 was transduced with the PHB genes ABC5KAN from MBX1164 to yield *E. coli* strain MBX 1329. MBX1164 is MBX247::ABC5KAN (encoding the thiolase, reductase and PHB synthase from *Z ramigera*). MBX247 is LJ5218 (Spratt, et al. 1981 J. Bacteriol. 146:1166–1169) *E. coli* genetic stock center CGSC 6966) mutagenized with 1-methyl-3-nitro-1-nitrosoguanidine (NTG) by a standard procedure (Miller, J., A short course in bacterial genetics, 1992, Cold Spring Harbor Laboratory Press, Cold Spring Harbor, N.Y.), and screened for the ability to grow with 1,2-propanediol as sole carbon source. Strains of *E. coli* with this ability and methods for generation of such strains have been described previously (Sridhara et al., 1969, J. Bacteriol. 93:87). *E. coli* strain MBX1329 has both the capability to grow smith 1,2-propanediol as the sole carbon source and to synthesize PHB from carbon sources that generate acetyl-CoA.

MBX1329 harboring plasmid pFS44C (shown in FIG. 2) was grown in a medium containing, per liter: 6.25 g LB broth powder; 3.5 g sodium ammonium phosphate; 7.5 g dibasic potassium phosphate trihydrate; 3.7 g monobasic potassium phosphate; 0.12 g magnesium sulfate; 2.78 mg iron (II) sulfate heptahydrate; 1.98 mg manganese (II) chloride tetrahydrate; 2.81 mg cobalt (II) sulfate heptahydrate; 1.47 mg calcium chloride dihydrate; 0.17 mg copper (II) chloride dihydrate; 0.29 mg zinc (II) chloride heptahydrate; 10 mg thiamine; 10 g 1,2-propanediol; 50 nmol coenzyme B-12; 100 µg ampicillin; and 0.05 mmol isopropyl-β-D-thiogalactopyranoside (IPTG). The total volume was 50 mL in a 250-mL Erlenmeyer flask; the inoculum was 0.5 mL of an overnight culture in 25 g/L LB broth powder and 100 µ/mL ampicillin. The cells were incubated in this medium for 3 days at 37° C. with shaking at 200 rpm. They were removed from this medium by centrifugation (2000×g, 10 minutes), washed once with water, centrifuged again, and lyophilized.

Intracellular polymer content was analyzed by butanolysis as in Example 1. The cells grew to an optical density (at 600 nm) of 9.8 and contained PHBV to 6% of the dry cell weight. The polymer itself was composed of 2.5% 3-hydroxyvalerate units and 97.5% 3-hydroxybutyrate units.

EXAMPLE 3

Poly(3-hydroxypropionate) from 1,3-propanediol and 1,3-propanediol from glycerol

Figure 3:
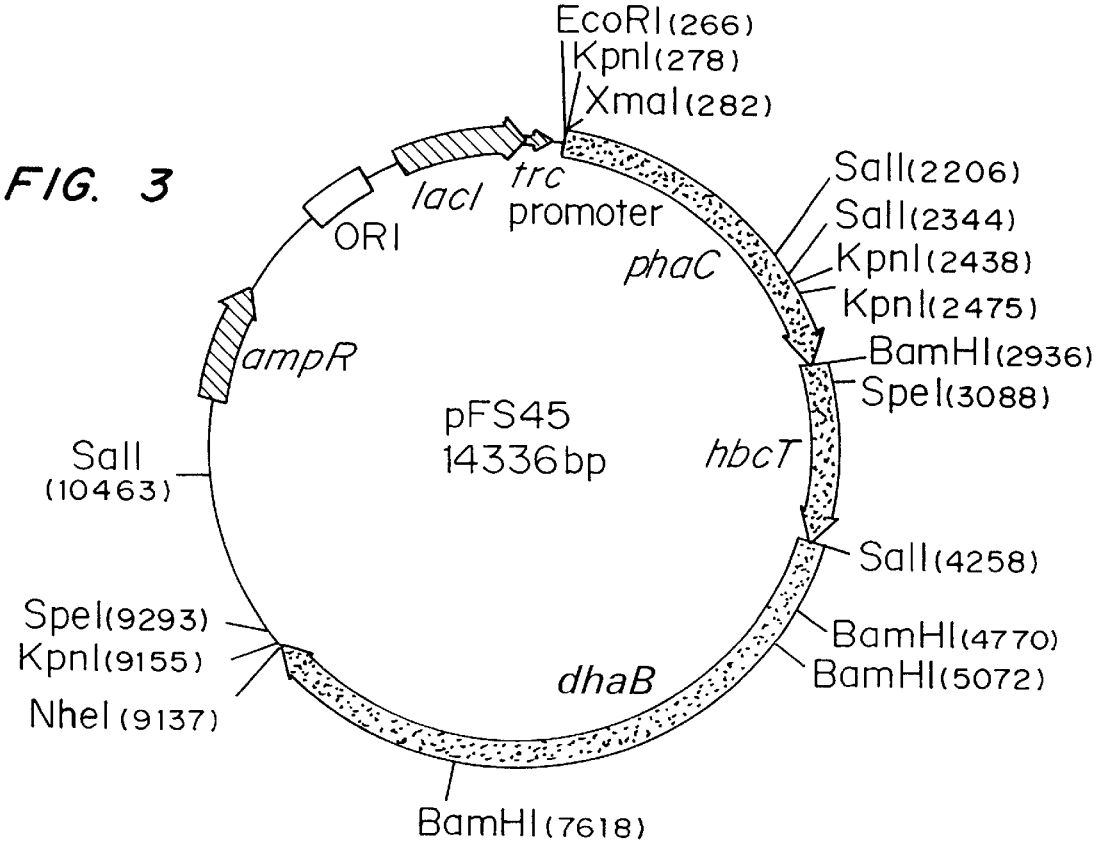
FIG. 3 is a schematic of the plasmid construct pFS45 encoding dhaB, hbcT and phaC.

*Escherichia coli* strain MBXI 184, which is deficient in the fadR gene and expresses the atoC gene constitutively, was used to synthesize 1,3-propanediol from glycerol and poly(3-hydroxypropionate) from 1,3-propanediol. In both instances the cells harbored plasmid pFS45 (shown schematically in FIG. 3) which contains genes encoding *Klebsiella pneumoniae* glycerol dehydratase, *Clostridium kluyveri* 4-hydroxybutyryl-CoA transferase, and *Ralstonia eutropha* PHA synthase, all in one operon under the control of the trc promoter. The cells were cultivated as described in Example 1, except that glycerol was present instead of 1,2-propanediol.

HPLC analysis showed that the cells in the coenzyme-B12-containing medium synthesized 1.3 g/L of 1,3-propanediol while the cells in the medium free of coenzyme B-12 did not synthesize any 1,3-propanediol. The same strain was also cultivated using the method of Example 1 except that 1,3-propanediol was present instead of 1,2-propanediol, and no coenzyme B-12 was added.

Lyophilized cell mass was analyzed by GC as in Example 1, with an additional standard of beta-propiolactone to quantify poly(3-hydroxypropionate). These cells were shown by GC analysis to contain poly(3-hydroxypropionate) homopolymer at 7.8% of the dry cell weight. The synthesis of poly(3-hydroxypropionate) from glycerol likely did not occur because of the accumulation of 3-hydroxypropionaldehyd(e, which is very toxic to many microorganisms (Dobrogosz et al., 1989, Wenner-Gren Int. Symp. Ser. 52:283–292). This toxicity may be addressed by discouraging the accumulation of 3-hydroxypropionaldehyde in at least two ways: 1) a 1,3-propanediol oxidoreductase from a 1,3-propanediol-producing organism such as those mentioned above can also be expressed, and 2) the activity of the unidentified endogenous dehydrogenase from *Escherichia coli* that is responsible for the observed formation of 1,3-propanediol when glycerol dehydratase is present can be increased by screening for *Escherichia coli* cells expressing glycerol dehydratase that grow well in the presence of both glycerol and coenzyme B-12. The second approach can be accomplished, for example, by transforming mutagenized *Escherichia coli* with a plasmid such as pFS45, so that the mutagenesis does not affect the glycerol dehydratase gene, followed by enrichment in a medium containing glycerol and coenzyme B-12.

EXAMPLE 4

Poly(3-hydroxypropionate) from glycerol

Figure 4:
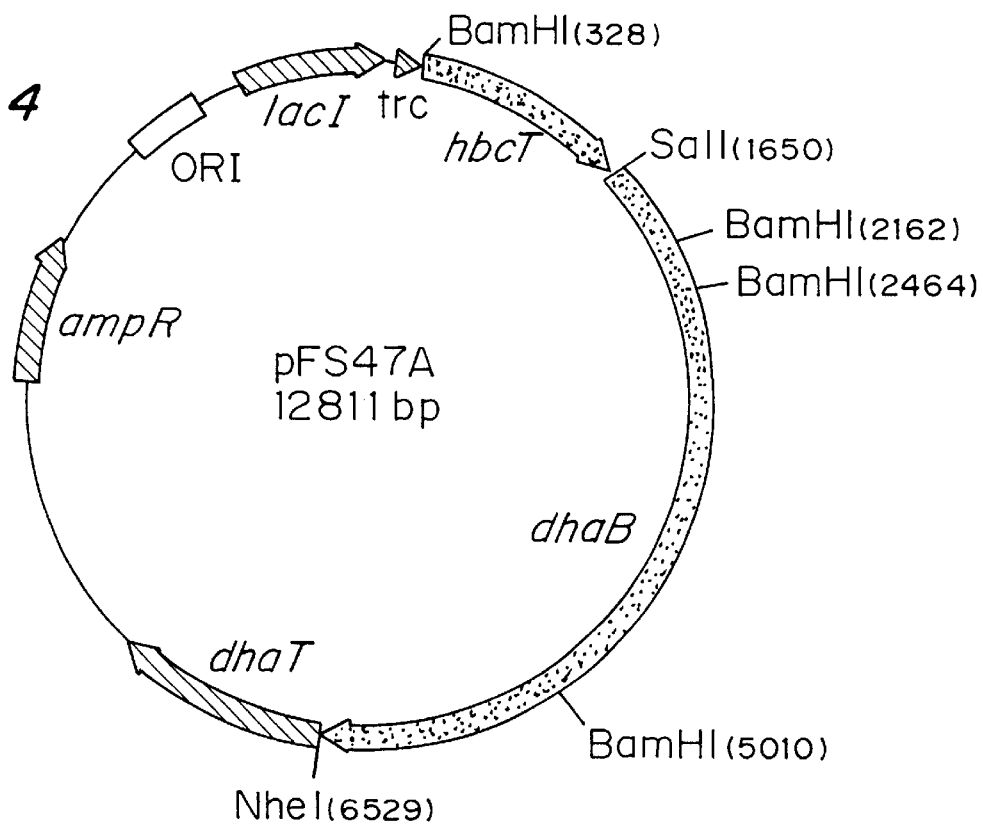
FIG. 4 is a schematic of the plasmid construct pFS47A, encoding dhaT, dhaB, and hbcT.
Figure 5:
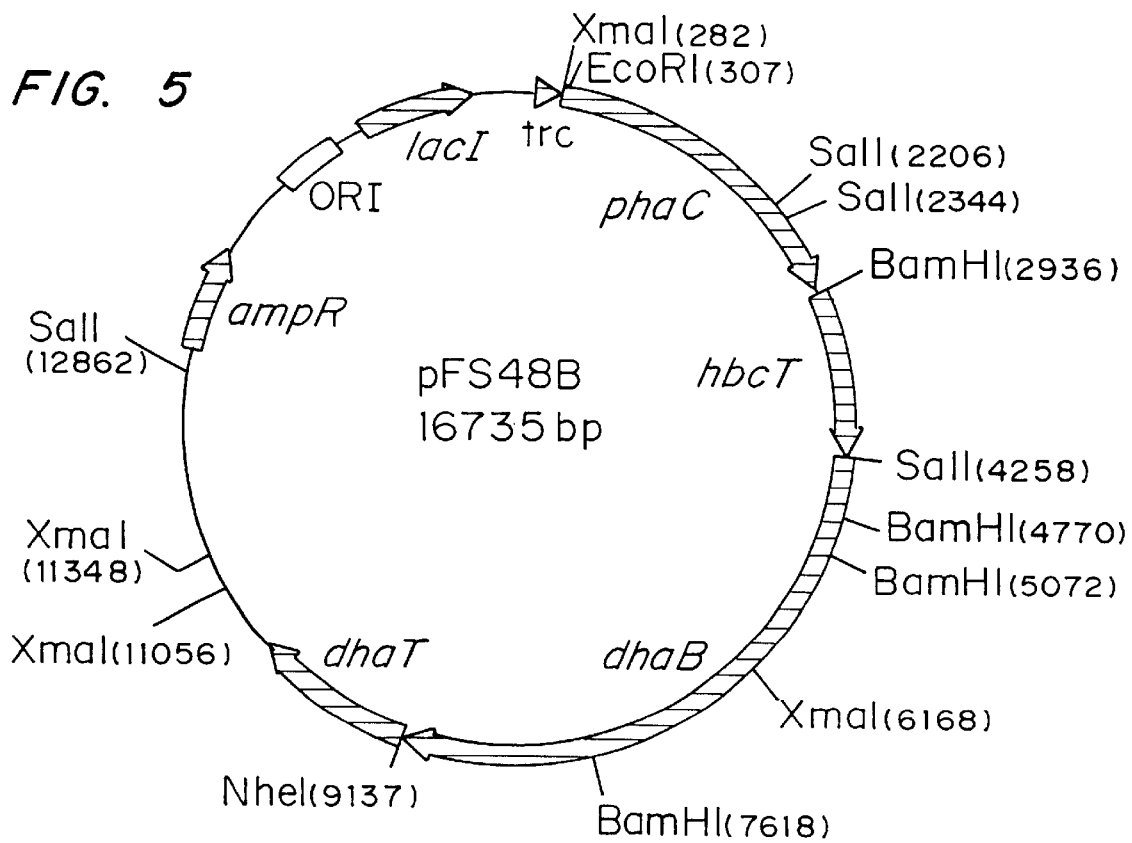
FIG. 5 is a schematic of the plasmid construct pFS48B, encoding dhaT, dhaB, hbcT, and phaC.

The two pathways in Example 3 (glycerol to 1,3-propanediol and 1,3-propanediol to poly(3-hydroxypropionate) were activated in the same recombinant *Escherichia coli*. E. coli strain MBX820, which stably expresses the PHA biosynthetic genes phaA, phaB, and phaC from *Zoogloea romigera*, was transformed with the plasmid pFS47A (shown schematically in FIG. 4), which contains, under control of the trc promoter, the genes encoding 4-hydroxybutyryl-CoA transferase from *Clostridium kluyveri* and glycerol dehydratase and 1,3-propanediol oxidoreductase from *Klebsiella pneumoniae*. PFS47A was constructed from the plasmid pFS 16, a predecessor of pFS47A, as follows: The *Closiridium kluyveri* orfZ gene was amplified by PCR from plasmid pCK3 (Söhling and Gottschalk, 1996, J. Bacteriol. 178: 871–880) using the following oligonucleotide primers:

```
5'-TCCCCTAGGATTCAGGAGGTTTTTATGGAGTGGGAAGAGATATATAAAG-3'   (SEQ ID NO:1)
(orfZ 5' AvrII)

5'-CCTTAAGTCGACAAATTCTAAAATCTCTTTTTAAATTC-3'             (SEQ ID NO:2)
(orfZ 3' SalI)
```

The orfZ PCR product was ligated to pTrcN, which had been digested with XbaI (which is compatible with AvrII) and SalI.

The cells were precultuied in 100 mL of a medium containing 25 g/L of LB broth powder (Difco; Detroit, Mich.) and 100 mg/L ampicillin. They were removed from this medium by centrifugation (2000×g, 10 minutes) and resuspended in 100 mL of a medium containing, per liter: 2.5 g LB broth powder; 50 mmol potassium phosphate, pH 7; 5 g substrate (glycerol; 1,2-propanediol; or 1,3-propanediol); 2 g glucose; 5 nmol coenzyme B-12; 100 µg ampicillin; and 0.1 mmol isopropyl-o-Dthiogalactopyranoside (IPTG). The cells were incubated in this medium with shaking at 225 rpm at 30° C. for 48 hours. They were then removed by centrifugation as above, washed once with water, and lyophilized.

The lyophilized cell mass was analyzed by GC analysis as in Example 1, with an additional standard of beta-propiolactone to quantify poly(3-hydroxypropionate). The cells cultivated in glycerol and 1,3-propanediol both contained a copolymer of 3-hydroxybutyrate and 3-hydroxypropionate units, and the cells cultivated in 1,2-propanediol contained a copolymer of 3-hydroxybutyrate and 3-hydroxyvalerate units. Polymer compositions and quantities as a percentage of dry cell weight are given in Table 1. The glycerol-cultivated cells synthesized more polymer than the 1,3-propanediol-cultivated cells, but the percentage of 3hydroxypropionate units was smaller in the glycerol-cultivated cells. These differences may be explained by the fact that 3-hydroxypropionaldehyde is toxic and that it is probably generated more quickly by 1,3-propanediol oxidoreductase from 1,3-propanediol than it is by glycerol dehydratase from glycerol. The toxicity of 3-hydroxypropionaldehyde can negatively impact cell health and therefore overall polymer conterit, but its formation from glycerol is necessary for 3-hydroxypropionyl-CoA formation whether the necessary intermediate is 3-hydroxypropionaldehyde or 1,3-propanediol.

Table 2 shows the amounts and compositions of the PHAs produced in this way. The absence of coenzyme B-12, whether the substrate was glycerol or 1,2-propanediol, resulted in synthesis of only PHB. Glycerol was more conducive to PHA formation in the absence of dehydratase activity, as shown by the final optical density and polymer content, presumably because *E. coli* can utilize glycerol as a carbon and energy source under aerobic conditions (Lin, Ann. Rev. Microbiol. 30:535, 1976), while generally this is

TABLE 1

Polymers produced by MBX820/pFS47A cultivated in various substrates.

| Substrate | Total polymer (% of dcw[a]) | 3HB units (% of polymer) | 3HP units (% of polymer) | 3HV units (% of polymer) |
|---|---|---|---|---|
| glycerol | 55.8 | 98.2 | 1.8 | 0.0 |
| 1,2-propanediol | 41.3 | 97.1 | 0.0 | 2.9 |
| 1,3-propanediol | 26.7 | 95.1 | 4.9 | 0.0 |

[a]percent of dry cell weight.

EXAMPLE 5

Control of polymer composition by variation of coenzyme B-12 concentration

Because the vicinal diol dehydratases depend upon coenzyme B-12 for activity, and because the formation of 3-hydroxypropionyl-CoA from glycerol or of propionyl-CoA from 1,2-propanediol depends upon dehydratase activity, the composition of the copolymer in either case can be controlled by variation of the availab,ility of coenzyme B-12 to the dehydratase. In this example, this was accomplished by variation of coenzyme B-12 concentration added to the medium in which *E. coli* strain MBX820 carrying the plasmid pFS47A was producing PHA.

The cells were precultured in 100 mL of a medium containing 25 g/L of LB broth powder (Difco; Detroit, Mich.) and 100 mg/L ampizillin. They were removed from this medium by centrifugation (2000×g, 10 minutes) and resuspended in 100 mL of a medium containing, per liter: 2.5 g LB broth powder; 50 mmol potassium phosphate, pH 7; 10 g substrate (glycerol or 1,2-propanediol); 2 g glucose; 100 μg ampicillin; 0.1 mmol isopropyl-β-D-thiogalactopyranoside (IPTG); and 0, 5, 20, or 50 nmol coenzyme B-12. The cells were incubated in this medium with shaking at 225 rpm at 30° C. for 72 hours. They were then removed by centrifugation as above, washed once with water, and lyophilized. The lyophilized cell mass was analyzed by GC analysis as in Example 4.

not true of 1,2-propanediol (Baldomá and Aguilar, ibid.). When coenzyme B-12 is added in increasing amounts to cells cultivated with glycerol, the percentage of 3-hydroxypropionate units in the polymer increases, while the overall polymer content decreases. This decrease is probably due to the toxicity of 3-hydroxypropionaldehyde, which results in decreased health of the cells. When coenzyme B-12 is added in increasing amounts to cells cultivated with 1,2-propanediol, 3-hydroxyvalerate units are incorporated into the polymer, but the percentage of 3-hydroxyvalerate in the polymer does not increase to the same extent as the percentage of 3-hydroxypropionate units did in the glycerol experiment. This indicates that the concentration of coenzyme B-12 is not limiting to 3-hydroxyvaleryl-CoA synthesis when its concentration reaches even a few nanomolar, and that some other factor becomes limiting.

This example demonstrates that the composition of PHAs derived from the use of coenzyme B-12-dependent dehydratases can be controlled by varying the concentration of coenzyme B-12 made available to the dehydratase. The extent to which the control can be executed is dependent on the diol substrate used. This can be due to the preference of the vicinal diol for certain substrates over others and on the rest of the host metabolism leading from the aldehyde derived from the diol to the acyl-CoA which serves as the activated monomer for PHA formation.

TABLE 2

Composition of polymers produced by MBX820/pFS47A from glycerol and 1,2-propanediol in media with various coenzyme B-12 concentrations.

| Substrate | [CoB12], nM | OD[a] (600 mn) | 3HB[b], % of PHA | 3HV[c], % of PHA | 3HP[d], % of PHA | polymer, % of dcw[e] |
|---|---|---|---|---|---|---|
| glycerol | 0 | 19.3 | 100 | 0 | 0 | 65.4 |
|  | 5 | 17.7 | 81.4 | 0 | 18.6 | 56.6 |
|  | 20 | 10.0 | 79.6 | 0 | 20.4 | 45.9 |
|  | 50 | 3.9 | 54.4 | 0 | 45.6 | 12.0 |
| 1,2-propanediol | 0 | 4.4 | 100 | 0 | 0 | 34.1 |
|  | 5 | 4.8 | 98.6 | 1.4 | 0 | 32.4 |
|  | 20 | 3.9 | 97.6 | 2.4 | 0 | 19.5 |
|  | 50 | 4.2 | 98.5 | 1.5 | 0 | 21.2 |

[a]optical density
[b]3-hydroxybutyrate units

TABLE 2-continued

Composition of polymers produced by MBX820/pFS47A from glycerol and 1,2-propanediol in media with various coenzyme B-12 concentrations.

| Substrate | [CoB12], nM | $OD^a$ (600 mn) | $3HB^b$, % of PHA | $3HV^c$, % of PHA | $3HP^d$, % of PHA | polymer, % of $dcw^e$ |
|---|---|---|---|---|---|---|

[c] 3-hydroxyvalerate units
[d] 3-hydroxypropionate units
[e] percent of dry cell weight

EXAMPLE 6

Production of poly(3-hydroxypropionate) from central metabolic intermediates Examples 1–5 demonstrate that it is possible to obtain poly(3-hydroxypropionate) from glycerol, and, as discussed above, it is possible in both transgenic and nontransgenic organisms to produce glycerol from central metabolic intermediates. Therefore, a combination of the two pathways will allow the synthesis of poly(3-hydroxypropionate) from central metabolic intermediates. These pathways can be combined either by introducing the poly(3-hydroxypropionate) synthesis genes into a glycerol-producing host or by introducing glycerol synthesis genes into a host already capable of poly(3-hydroxypropionate) synthesis from glycerol, such as described in the above examples.

In the former case, genes encoding a vicinal diol dehydratase, a PHA synthase, and optionally an aldehyde dehydrogenase, 1,3-propanediol oxidoreductase, and hydroxyacyl-CoA transferase are expressed in a host capable of producing glycerol from central metabolic intermediates. An example of such a host is an *Escherichia coli* that expresses the *Saccharomyces cerevisiae* DAR1 (dihydroxyacetone phosphate dehydrogenase) and GPP2 (sn-glycerol-3-phosphate phosphatase) genes (Anton, D. "Biological production of 1,3-propanediol", presented at United Engineeing Foundation Metabolic Engineering II conference, Elmau, Germany, Oct. 27, 1998; PCT WO 98/21339), as described above. Many strains of *E. coli* naturally express 1,3-propanediol oxidoreductase and aldehyde dehydrogenase enzymatic activities, but their levels may optionally be augmented by mutagenesis or purposeful overexpression of enzymes that carry out these functions. The additional genes necessary can be introduced on a plasmid such as pFS48B, which contains, under the control of the trc promoter, 4-hydroxybutyryl-CoA transferase from *Clostridium kluyveri*; PHA synthase from *Zoogloea ramigera* and glycerol dehydratase and 1,3-propanediol oxidoreductase from *Klebsiella pneumoniae*. Any or all of these genes may also be introduced by integration into the chromosome using standard techniques well-known to those skilled in the art.

Similarly, the DAR1 and GPP2 genes can be introduced into a host already capable of poly(3-hydroxypropionate) synthesis, such as MBX820 pFS47A, described above. The DAR1 and GPP2 genes may be introduced on a plasmid compatible with pFS47A (a plasmid that can be maintained simultaneously with pFS47A), or they may be integrated into the chromosome. MBX820 stably expresses acetoacetyl-CoA thiolase, 3-hydroxybutyryl-CoA reductase, and PHA synthase, and therefore it is capable of synthesizing poly(3-hydroxybutyrate-co -3-hydroxypropionate). If the homopolymer poly(3-hydroxypropionate) is desired, a strain expressing only PHA synthase rather than all three PHB biosynthetic genes may be used.

Figure 6:
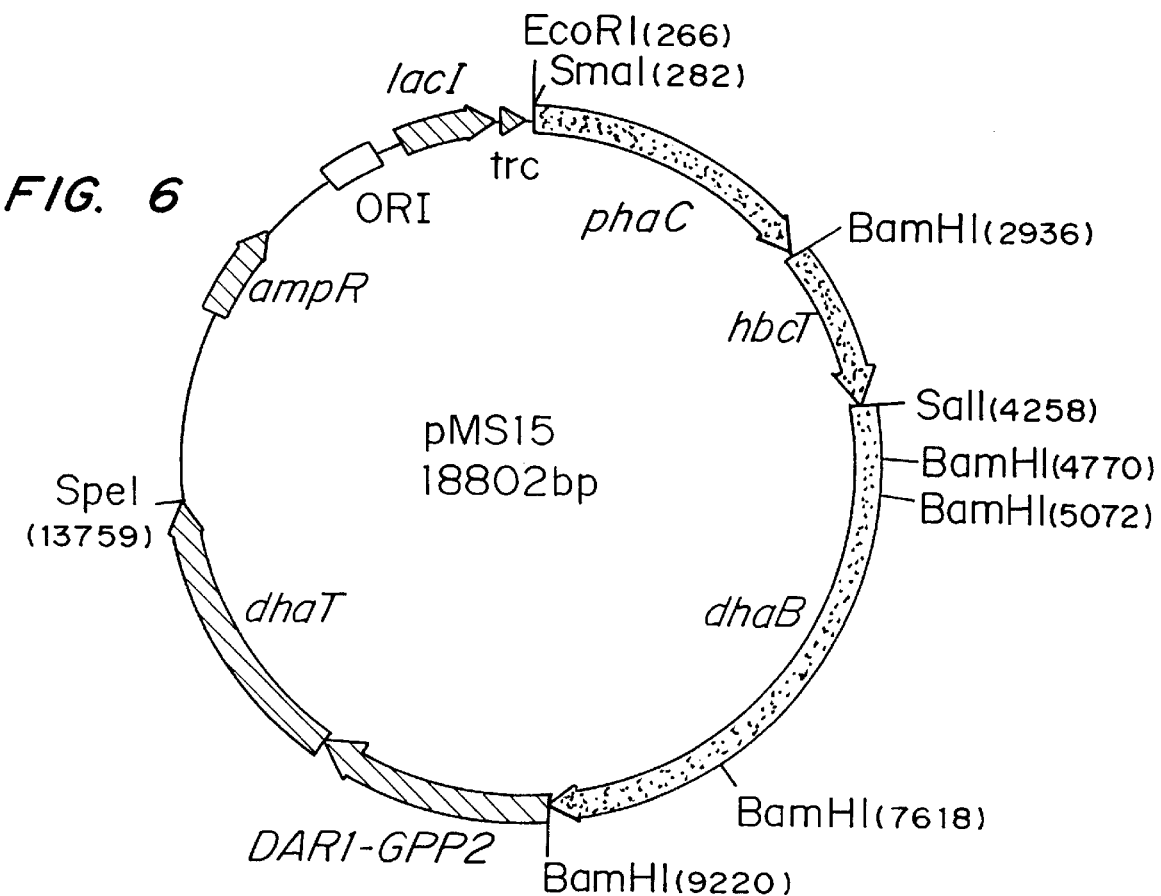
FIG. 6 is a schematic of the plasirid construct pMS15, encoding dhaT, DAR1-GPP2 (DAR1,dihydroxyacetone phosphate dehydrogenase; and GPP2, sn-glycerol-3-phosphate phosphatase), dhab, hbcT, and phaC.
Figure 7:
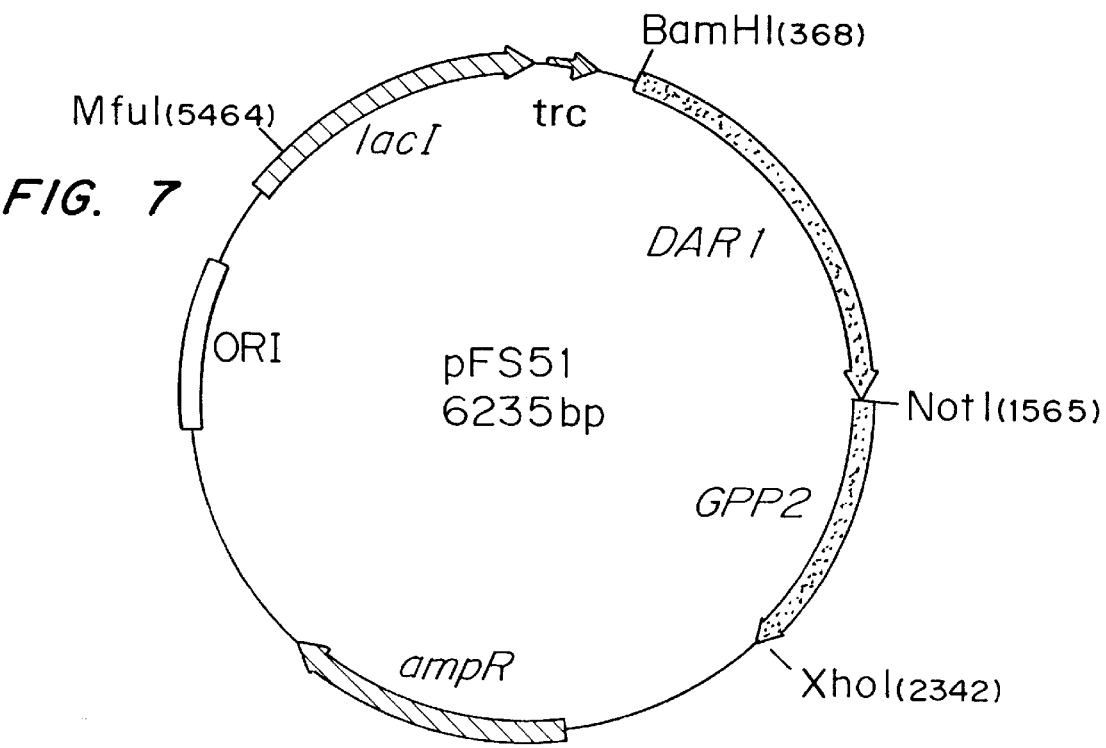
FIG. 7 is a schematic of the plasmid construct pFS51, encoding GPP2 and DAR1.

In order to demonstrate the pathway for the biosynthesis of PHP form glucose, plasmid pMS 15 (shown schematically in FIG. 6) was constructed to express the following genes as an operon from the trc promoter: PHB synthase from *A. eutrophus*, the 4-hydroxybutyryl-CoA transferase from *C. kluyveri*, the glycerol dehydratase from *Klebsiella*, the DAR1 gene from *S. cerevisae*, the GPP2 gene from *S. cerevisae* and the 1,3-propanediol oxidoreductase from *K pneumoniae*.

The plasmid pFS51 was constructed by ligating DAR1 and GPP2 PCR products one at a time to pTrcN. The DAR1 gene was amplified by PCR from *S. cerevisiae* genomic DNA using the following oligonucleotide primers:

```
5'-CTTCCGGATCCATTCAGGAGGTTTTTATGTCTGCTGCTGCTGATAGA-3'        (SEQ ID NO:3)
(S. cer. DAR1 5' BamHI)

5'-CTTCCGCGGCCGCCTAATCTTCAfGTAGATCTAATTC-3'                  (SEQ ID NO:4)
(S. cer. DAR1 3' NotI)

The GPP2 gene was amplified in the same way using the
following oligonucleotide primers:

5'-CTTCCGCGGCCGCATTCAGGAGGTTTTTATGGGATTGACTACTAAACCTC-3'    (SEQ ID NO:5)
(S. cer. GPP2 5' NotI)

5'-CCTTCTCGAGTTACCATTTCAACAGATCGTCC-3'                      (SEQ ID NO:6)
(S. cer. GPP2 3' XhoI)
```

PCR for each gene was carried out with Pfu DNA polymerase (Stratagene; La Jolla, Calif.) in a reaction volume of 50 μL, which contained: 10 units Pfu polymerase, 1× reaction buffer provided by the manufacturer, 50 pmol of each primer, about 200 ng *S. cerevisiae* genomic DNA, and 200 μM of each dNTP. The thermal profile of the reactions was as follows: 27 cycles of(94° C., 1 min; 55° C., 2 min; 72° C., 3 min), then 7 min at 72° C. The Pfu polymerase was not added until the reaction mixture had reached 94° C.

The PCR products were purified from a 1% low-melt agarose gel and digested with the restriction enzymes whose corresponding sites had been included at the 5' ends of the primers (BamHI and NotI for DAR1, NotI and XhoI for GPP2). The vector pTrcN is a version of pTrc99a (Pharmacia; Uppsala, Sweden) modified such that it lacks an NcoI site. pTrcN was cut with BamHI, NotI, and calf intestinal alkaline phosphatase (CIAP; Promega; Madison, Wis.) for insertion of DAR1 and with NctI, AhoI, and CIAP for insertion of GPP2. The ligations were carried out with T4 DNA ligase (New England Biolabs; Beverly, Mass.) according to the instructions provided by the manufacturer. The products of the ligations were pFS49 (DAR1) and pFS50 (GPP2). To assemble both genes on one plasmid, pFS49 was cut with MluI and NotI, and the 2.3-kb fragment containing the trc promoter and DAR1 was ligated to pFS50 that had been digested with the same two enzymes and CIAP. The resulting plasmid, which contained the operon DAR1-GPP2 under control of the trc promoter, was denoted pFS51.

E. coli strain MBX 184 containing the plasmid pMS 15 (shown schematically in FIG. 6) was grown overnight in a 200-mL square bottle at 37° C. in 50 mL of LB medium which also contained 100 µg/mL ampicillin. The cells were removed from this culture by centrifugation for 10 minutes at 2000×g, and the cells were resuspended in 50 mL of a glucose medium and incubated for 72 hours at 30° C. with shaking at 200 rpm. The glucose medium contained, per liter: 6.25 g LB powder; 100 µg ampicillin; 20 g glucose; 50 mmol potassium phosphate, pH 7; 10 µmol isopropyl-β-D-thiogalactopyranoside (IPTG); and 0, 10, or 100 nmol coenzyme B-12. After the incubation, the cells were removed from the medium by centrifugation for 10 minutes at 2000×g, washed once with water and centrifuged again, then lyophilized. Gas chromatographic (GC) analysis of the lyophilized cell mass showed that, in the experiment with 10 nM coenzyme B-12, poly(3HP) made up 0.11% of the dry cell weight; in the experiment with 100 nM coenzyme B-12, poly(3HP) made up 0.13% of the dry cell weight; and in the experiment with no coenzyme B-12, poly(3HP) was not detected. No polymer constituents other than 3HP were found in any case. GC analysis was conducted as follows: 15 to 20 mg of lyophilized cell mass was subjected to simultaneous extraction and propanolysis at 100° C. for 3 hours in 2 mL of a mixture containing (by volume) 50% 1,2-dichloroethane, 40% 1-propanol, and 10% concentrated hydrochloric acid, with 2 mg/mL benzoic acid added as an internal standard. The water-soluble components of the resulting mixture were removed by extraction with 3 mL water. The organic phase (1 µL at a split ratio of 1:50 at an overall flow rate of 2 mL/min) was analyzed on an SPB-1 fused silica capillary GC column (30 m; 0.32 mm ID; 0.25 µm film; Supelco; Bellefonte, Pa.) with the following temperature profile: 80° C. for 2 min; 10° C. per min to 250° C.; 250° C. for 2 min. The standard used to test for the presence of 3HP residues was β-propiolactone. Both poly(3HP) and β-propiolactone yield the 1-propyl ester of 3-hydroxypropionate when subjected to propanolysis.

EXAMPLE 7

PHBV from central metabolic intermediates

As demonstrated above, it is possible to obtain PHBV from 1,2-propanediol with the optional addition of other carbon sources such as glucose, and it is possible in both transgenic and nontransgenic organisms to produce 1,2-propanediol from central metabolic intermediates (Cameron et. al., 1998, Biotechnol. Prog. 14 116–125). Therefore, a combination of the two pathways will allow the synthesis of PHBV from central metabolic intermediates. These pathways can be combined either by introducing the PHBV synthesis genes into a 1,2-propanediol-producing host or by introducing 1,2-propanediol synthesis genes into a host already capable of PHBV synthesis from 1,2-propanediol, such as described in the above examples.

In the former case, genes encoding a vicinal diol dehydratase, a PHA synthase, a 3-ketoacyl-CoA thiolase and reductase, and optionally an aldehyde dehydrogenase, 1-propanol oxidoreductase, and hydroxyacyl-CoA transferase are expressed in a host capable of producing 1,2-propanediol from central metabolic intermediates. An example of such a host is an *Escherichia coli* that expresses rat lens aldose reductase or overexpresses E. coli glycerol dehydrogenase, as described above. Many strains of E. coli naturally express 1-propanol oxidoreductase, aldehyde dehydrogenase, and propionyl-CoA transferase enzymatic activities, but their levels may optionally be augmented by mutagenesis or purposeful overexpression of enzymes that carry out these functions. The additional genes necessary can be introduced as plasmid-boine genes or may be integrated into the chromosome, or a combination of the two approaches may be used. For example, a plasmid such as pFS48B, which contains, under the control of the trc promoter, 4-hydroxybutyryl-CoA transferase from *Clostridium kluyveri*; PHA synthase from *Zoogloea ramigera* and glycerol dehydratase and 1,3-propanediol oxidoreductase from *Klebsiella pneumoniae*, may be used in combination with integration of the PHB synthesis genes into the chromosome using standard techniques well-known to those skilled in the art.

Similarly, the rat lens aldose reductase or E. coli glycerol dehydrogenase genes can be introduced into a host already capable of PIIBV synthesis, such as MBX769/pFS44C, described above. An additional improvement may result from the overexpression of a methylglyoxal synthase gene, as suggested by Cameron et al., 1998 (Biotechnol. Prog. 14 116–125). The rat lens aldose reductase or E. coli glycerol dehydrogenase gene may be introduced on a plasmid compatible with pFS44C (a plasmid that can be maintained simultaneously with pFS44C), or they may be integrated into the chromosome.

EXAMPLE 8

Identification of 3-hydroxypropionaldehyde Dehydrogenase Activity

The aldH gene sequence from E. coli is available from GENBANK. This gene was cloned into the Acc651 and NotI sites of the cloning vector pSE380 following PCR amplification using the approach described in Example 6 and the following primers:

```
ald-Acc65I  5'-ggtggtaccttaagaggaggtttttatgaattttcatcacctggctt  (SEQ ID NO:7)

ald-NotI    5'-ggtgcggccgctcaggcctccaggcttatcca               (SEQ ID NO:8)
```

The resulting recombinant plasmid TALDH was introduced into E. coli DH5 alpha and grown in 5 ml LB medium with 100 µg/ml ampicillin 37° C. The next day a 100 ml containing 100 µg/ml ampicillin was innoculated with 100µl of the overnight culture and grown until the absorbance at 600 nm reached 0.5 at which time the trc promoter was induced with 1 mM IPTG and incubated a further 3 hours at 37° C. The cells were harvested, washed and resuspended in 0.1 M Tris.HCI pH 8.0 and lysed by sonication. The cell lysate was assayed for aldehyde dehydrogenase activity using 3-hydroxypropionaldehyde with both AND and NADP as cofactor. Assays were performed using an Hewlett Packard diode array spectrophotometer. Enzyme reactions were carried out in 1 5 ml UV cuvettes in a solution containing the following: 0.1 M Tris .Hcl, pH 8.0, 1 mM AND or NADP, 6 mM dithiothreitol and crude cell extract to a final volume of 1 ml. The mixture was incubated for 20 seconds before initiating the reaction by adding 1 mM 3-hydroxypropionaldehyde and monitoring the reaction at 340 nm. The lysate showed significant 3-hydroxypropionaldehyde dehydrogenase activity when AND was the cofactor (1.35 μmoles/min/mg protein) which was not present in the control sample prepared using the vector alone. Therefore the aldH gene can be used to increase the 3-hydroxyproionaldehyde dehydrogenase activty in the strains described in the previous examples.

We claim:

1. A method for producing polyhydroxyalkanoates comprising providing organisms which express enzymes selected from the group consisting of acyl-CoA transferase, acyl-CoA synthetase, β-ketothiolase, acetoacetyl-CoA reductase, and polyhvdroxyalkanoate synthase, and which are genetically engineered to express enzymes selected from the group consisting of dehydratases glycerol-3-phosphate dehydrogenase and glycerol-3-phosphatase,
    providing diols which can be converted into 3-hydroxypropionate or 3-hydroxyvalerate monomers by enzymes expressed by tile organisms, and
    culturing the organisms under conditions wherein 3-hydroxypropionate or 3-hydroxyvalerate is polymerized to form polyhydroxyalkanoates.

2. The method of claim 1 wherein the organisms are bacteria.

3. The method of claim 1 Wherein the organisms are plants.

4. The method of claim 1 wherein the organisms are genetically engineered with plasmids encoding one or more of the enzymes.

5. The method of claim 1 wherein the organisms are genetically engineered to incorporate the genes encoding the enzymes into the chromosome.

6. The method of claim 1 wherein the diols are selected from the group consisting of 1,2-propanediol, 1,3 propanediol and glycerol.

7. The method of claim 1 wherein the dehydratases are selected from the group consisting of glycerol dehydratase and diol dehydratase.

8. The method of claim 1 further comprising providing genes encoding an enzyme selected from the group consisting of aldehyde dehydrogenase and 1,3-propanediol oxidoreductase.

9. A system for making polyhydroxyalkanoates comprising an organism expressing enzymes selected from the group consisting of acyl-CoA transferase, acyl-CoA synthetase., β-ketothiolase, acetoacetyl-CoA reductase, and polyhydroxiyalaoate synthase, wherein the orpanism is genetically engineered to express enzymes selected from the group consisting of dehydratases, glycerol-3-phosphate dehydrogenase and glycerol-3-phosphatsse,
    wherein the organism can convert diols into 3-hydroxypropionate or 3-hydroxyvalerate monomers which are polymerized to form polyhydroxyalkanoates.

10. The system of claim 9 wherein the organisms are bacteria.

11. The system of claim 9 wherein the organisms are plants.

12. The system of claim 9 wherein the organisms are genetically engineered with plasmids encoding one or more of the enzymes.

13. The system of claim 9 wherein the organisms are genetically engineered to incorporate the genes encoding the enzymnes into the chromosome.

14. The system of claim 9 further comprising coenzyme B-12.

15. The system of claim 9 wherein the vicinal diol dehydratase is selected from the group consisting of glycerol dehydratase and diol dehydratase.

16. The system of claim 9 further comprising genes encoding an enzyme selected from the group consisting of aldehyde dehydrogenase and 1,3-propanediol oxidoreductase.

* * * * *

UNITED STATES PATENT AND TRADEMARK OFFICE
CERTIFICATE OF CORRECTION

PATENT NO. : 6,329,183 B1
DATED : December 11, 2001
INVENTOR(S) : Frank A. Skraly and Oliver P. Peoples It is certified that error appears in the above-identified patent and that said Letters Patent is hereby corrected as shown below:

Title page,
Item [57], ABSTRACT,
Line 12, change "3-hydroxyvalreate" to -- 3-hydroxyvalerate --.

Column 3,
Line 47, change "enzymes" to -- enzyme --.

Column 4,
Line 12, change "oe" to -- be --.
Line 50, change "mutagenise" to -- mutagenize --.
Line 52, change "uider" to -- under --.
Line 64, change "engeneered" to -- engineered --.

Column 6,
Line 61, change "mcnomer" to -- monomer --.

Column 7,
Line 28, change "tfat" to -- that --.
Line 37, change "sevtral" to -- several --.
Line 57, change "*Zogloea*" to -- *Zoogloea* --.
Line 63, change "*kluzyveri*" to -- *kluyveri* --.
Line 67, change "lacl" to -- lacI --.

Column 8,
Line 3, change "La Jolla" to -- Carlsbad --.
Line 37, change "fimctional" to -- functional --.

Column 9,
Line 29, change "MBXI 184" to -- MBX184 --.
Line 62, change "3-hydroxypropionaldehyd(e" to -- 3-hydroxypropionaldehyde --.

UNITED STATES PATENT AND TRADEMARK OFFICE
CERTIFICATE OF CORRECTION

PATENT NO.    : 6,329,183 B1
DATED         : December 11, 2001
INVENTOR(S)   : Frank A. Skraly and Oliver P. Peoples It is certified that error appears in the above-identified patent and that said Letters Patent is hereby corrected as shown below:

Column 11,
Line 6, change "conterit" to -- content --.
Line 39, change "ampizillin" to -- ampicillin --.

Column 14,
Line 15, change "MBX820 pFS47A" to -- MBX820/pFS47A --.

Column 15,
Line 3, change "NctI, AhoI" to -- NotI, XhoI --.
Line 62, change "TALDH" to -- pALDH --.
Line 64, change "100 ml" to -- 100-mL culture --.
Line 65, change "innoculated" to -- inoculated --.
Lines 56-67, move Column 15, lines 56-67 to Column 16, after line 55 and before line 62.

Column 16,
Line 37, change "PIIBV" to -- PHBV --.
Line 66, change "AND" to -- NAD --.

Column 17,
Line 2, change "1 5" to -- 1.5 --.
Line 4, change "AND" to -- NAD --.

Column 18,
Line 3, change "AND" to -- NAD --.
Line 7, change "activty" to -- activity --.

Column 19,
Line 38, change "polyhvdroxyalkanoate" to -- polyhydroxyalkanoate --.
Line 40, change "dehydratases" to -- dehydratases, --.
Line 44, change "tile" to -- the --.

UNITED STATES PATENT AND TRADEMARK OFFICE
CERTIFICATE OF CORRECTION

PATENT NO. : 6,329,183 B1
DATED : December 11, 2001
INVENTOR(S) : Frank A. Skraly and Oliver P. Peoples It is certified that error appears in the above-identified patent and that said Letters Patent is hereby corrected as shown below:

<u>Column 20,</u>
Line 36, change "synthetase.," to -- synthetase, --.
Line 37, change "polyhydroxiyalaoate" to -- polyhydroxyalkanoate -- and change "orpanism" to -- organism --.
Line 40, change "phosphatsse" to -- phosphatase --.
Line 56, change "enzymnes" to -- enzymes --.

Signed and Sealed this

Twenty-fifth Day of March, 2003

JAMES E. ROGAN
*Director of the United States Patent and Trademark Office*